United States Patent [19]

Fiez Vandai

[11] Patent Number: 5,212,158
[45] Date of Patent: May 18, 1993

[54] DERIVATIVES OF L-PROLINE, THEIR PREPARATION AND THEIR BIOLOGICAL USES

[75] Inventor: Pierre-Yves Fiez Vandai, Chatou, France

[73] Assignee: Inorgan SA Recherche & Developpement Pharmaceutiques, CAS, Geneva, Switzerland

[21] Appl. No.: 266,680
[22] Filed: Nov. 3, 1988
[30] Foreign Application Priority Data Nov. 3, 1987 [FR] France ............................ 87 15228

[51] Int. Cl.$^5$ .................. C07K 5/08; A61K 37/02
[52] U.S. Cl. ........................................ 514/18; 530/331
[58] Field of Search .................... 530/331, 330, 338; 514/18

[56] References Cited

U.S. PATENT DOCUMENTS

| | | | |
|---|---|---|---|
| 4,691,007 | 9/1987 | Dutta et al. | 530/331 |
| 4,748,116 | 5/1988 | Simonsson et al. | 530/331 |
| 4,804,743 | 2/1989 | Kaltenbronn et al. | 530/331 |

FOREIGN PATENT DOCUMENTS

| | | | |
|---|---|---|---|
| 112597 | 5/1988 | Japan | 514/18 |
| 1523598 | 9/1978 | United Kingdom | |

OTHER PUBLICATIONS

Pitt, et al. Am J. Physiology, 1986 250 (5, Pt. 2) H806-H814 Chemical Abs. vol. 105, 1986, Abs. 4622p.
Venkata Chalapathi, et al Biopolymers 1981, 20(6) 1137-45 Chemical Abstracts vol. 95, 1981 Abstract 81511d.
Thompson, et al New England Journal of Medicine vol. 333 (7), 1990 pp. 445-448.
Marx, Science vol. 250 1990 pp. 1509-1410.
H. Shiraishi et al: "Taste of proline-containing peptides", Chemical Abstracts, vol. 80, 2974, n° 93707a, p. 233.
Pitt et al: "Effect of hypoxia and hypercapnia on ACE activity in the cerebral microcirculation of anesthetized dogs", Am. J. Physiol. 250 (Heart Circ. Physiol. 19) H806-H814, 1986.
Venkatachalapathi et al: "X-Pro Peptides: Synthesis and Solution Conformation of Benzyloxycarbonyl-(Aib-Pro),-Methyl Ester, Evidence for a Novel Helical Structure", Biopolymers, vol. 20, 1137-1145, (1981).
L. Sachs et al: "A highly specific aminotripeptidase of rats brain cytosol. Substrate specificity and effects of inhibitor", Chemical Abstracts, vol. 97, p. 270, n° 195014r, 1982.

Primary Examiner—Robert T. Bond
Assistant Examiner—E. C. Ward
Attorney, Agent, or Firm—Cushman, Darby & Cushman

[57] ABSTRACT

The L-proline derivatives of the invention correspond to the Formula I:

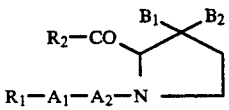

in which
$R_1$ corresponds to the Formula II:

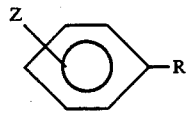

in which R is a carbonyl group, an acyl group —Y—CO— or an oxy-acyl group —O—Y—CO—, Y being an alkyl or an alkenyl chain, Z being one or more hydrogen atoms, or one or more substituents chosen from among halogen atoms, $CF_3$, alkyl or alkoxy groups and an alkylenedioxy group in the case of two neighbouring substituents,
$R_2$ is —$NH_2$, —OH, or a derivative of these groups,
$A_1$ and $A_2$ are amino acid residues and
$B_1$ and $B_2$ represents a hydrogen atom or a methyl group, and the pharmacologically acceptable salts of these derivatives.

These derivatives are useful particularly as the active principles of medicines possessing, in particular, a nootropic action.

18 Claims, No Drawings

DERIVATIVES OF L-PROLINE, THEIR PREPARATION AND THEIR BIOLOGICAL USES

The subject of the invention is novel derivatives of L-proline, their preparation and their biological uses.

The invention relates more particularly to derivatives of L-proline possessing a therapeutic activity, in particular a psychotropic activity and more especially a nootropic activity.

Known substances possessing a nootropic activity include ergot, the rye parasite, piracetam and certain peptide neurohormones. The inventor of the present patent application has observed that these substances possess a structural analogy and has attempted to design L-proline derivatives possessing, in particular, a nootropic effect but which do not possess the pharmacological activities of ergot associated with ergoline, which are more active than piracetam and which are active by the oral route.

The experiments carried out have led to the development of a family of derivatives of L-proline possessing the desired properties and which, in an advantageous manner, are active at low doses.

The L-proline derivatives of the invention are characterized in that they correspond to the Formula I

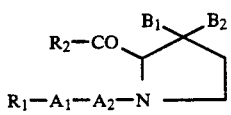

in which
R$_1$ is a group corresponding to Formula II

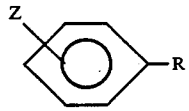

in which R is a carbonyl radical CO—, an acyl radical Y—CO— or an oxyacyl radical O—Y—CO—, in which Y is an alkyl or alkenyl chain of, in particular, from 1 to 4 carbon atoms, Z represents one or more hydrogen atoms, or one or more substituents in the ortho and/or ortho' and/or meta and/or meta' and/or para positions, chosen from among halogen atoms, a CF$_3$ group, alkyl or alkoxy radicals containing from 1 to 4 carbon atoms and in the case of two neighbouring substituents, an alkylenedioxy group, the alkylene group containing from 1 to 3 carbon atoms, R$_2$ is a NH$_2$ or OH radical, or functional derivatives of these radicals, A$_1$ and A$_2$, identical or different, are amino acid residues, and B$_1$ and B$_2$, identical or different, represent a hydrogen atom or a methyl group, and the pharmacologically acceptable salts of these derivatives.

In a preferred family, the Z substituent in the Formula II represents a hydrogen atom.

In another preferred family, the Z substituent is a halogen atom chosen from among chlorine and fluorine, a CF$_3$ group, an alkoxy radical chosen from among methoxy and ethoxy groups, and in the case of two neighbouring positions, an alkylenedioxy radical chosen from among 3,4-methylene and 3,4-ethylenedioxy radicals.

In these families, the R substituent is advantageously chosen from among the groups CO, CH$_2$—CO—, CH$_2$—CH$_2$—CO—, CH$_2$—CH$_2$—CH$_2$—CO—, CH=CH—CO— and O—CH$_2$—CO—.

A preferred group of derivatives of L-proline corresponding to the above families contain naturally occurring amino acids A$_1$ and A$_2$. In particularly useful substances, A$_1$ is chosen from among the residues glycine, L-alanine and L-valine, and A$_2$ is chosen from among the residues glycine, L-phenylalanine, L-histidine, L-leucine, L-valine and L-alanine.

The invention also relates to a process for the preparation of the derivatives of L-proline defined above.

This process is characterized by the fact that a derivative of Formula III

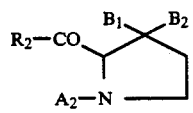

is made to react with a derivative of Formula IV

R$_1$—A$_1$                     (IV).

In these formulae, B$_1$, B$_2$, A$_1$, A$_2$, R$_1$ and R$_2$ are as defined above.

In order to prepare the derivative corresponding to Formula III it is advantageous to allow a derivative of proline corresponding to Formula V

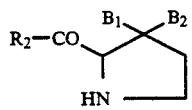

to react with an amino acid A$_2$.

The condensation reaction is preferably carried out at a temperature lower than room temperature, and more particularly lower than 0° C. Preferred temperatures are lower than −10° C., and in particular are of the order of −15° C.

The reaction is advantageously carried out in an organic solvent such as tetrahydrofuran (THF) or dimethylformamide (DMF).

The amine function of the amino acid A$_2$ used is advantageously protected by a group which can subsequently be removed by acids. The standard protecting groups employed in peptide synthesis are used such as the tertiary butoxycarbonyl, benzyloxycarbonyl or 9-fluorenylmethoxycarbonyl groups, or any other group used in peptide chemistry and considered to be appropriate by the expert.

The protecting group is removed advantageously under strongly acidic conditions in order to enable A$_2$ to be condensed with the proline derivative corresponding to Formula III. For this purpose, an anhydrous acid such as a solution of gaseous hydrogen chloride in an organic solvent, for example dioxane, is used.

Strongly acidic conditions in aqueous medium may also be used. As an example, the use of hydrochloric acid or sulfuric acid in concentrated aqueous solution may be mentioned.

The derivative R$_1$—A$_1$ of Formula IV is the product of the condensation of reactive derivatives of R$_1$ and A$_1$ (the carboxyl function of $A_1$ being blocked by a protecting group) followed by saponification by means of a strong base. The reactive derivatives of $R_1$ include for example the acyl halides, in particular the acyl chloride, the use of such reactive groups being permitted provided that there is no possibility of side-reactions with the derivatives of the protected amino acids used. The carboxyl function of $A_1$ is blocked by the protecting groups usually used in peptide synthesis. This function is preferably protected in the form of esters, in particular alkyl esters, the alkyl group possessing preferably from 1 to 4 carbon atoms, or as the benzyl ester. Advantageously, the esters of $A_1$ are available in the form of salts, for example their hydrochlorides.

The condensation step between the reactive derivatives is preferably carried out at a temperature lower than room temperature, preferably lower than $0°$ C., and in particular at a temperature of the order of $-5°$ C. to $-10°$ C.

The saponification step is carried out with a base in an organic solvent, in particular in an alcoholic solvent such as methanol. The reaction is advantageously carried out at room temperature.

When the product precipitates, the reaction mixture is adjusted to acid pH values, lower than 3, in particular lower than 2, and preferably of the order of 1.5.

The amino acids $A_1$ and $A_2$ used in the above condensation reactions are advantageously protected and activated with a view to coupling. Numerous methods can be used for this purpose.

Satisfactory results are obtained by using for example N-methylmorpholine to prepare the salt of the amino acid derivative which is then allowed to react with isobutyl chloroformate in order to form a carboxylic acid-carbonic acid mixed anhydride which is an activated derivative of the amino acid. In order to prevent side reactions resulting from the use of isobutyl chloroformate, an additive constituted advantageously by a triazole derivative, in particular 1-hydroxybenzotriazole, may be added.

Among the other standard methods used to activate the amino acids, with a view to coupling, mention will be made of use of active esters such as those derived in particular from N-hydroxysuccinimide, 4-nitrophenol, pentafluorophenol and analogues, as well as the use of coupling by means of carbodiimides, succinimides and analagous reagents.

The pharmacological study of the derivatives of L-proline of the invention demonstrated a high psychotropic activity. This activity was revealed particularly in pharmacological tests of passive avoidance commonly used to determine the potential activity of substances on memory in particular.

Thus, after amnesia has been induced by the absorption of scopolamine, it is observed that the substances of the invention are capable of correcting the amnesia thus induced and they do so at low doses, a feature of great importance.

Furthermore, the advantageous properties of the substances of the invention are accompanied by low toxicity. In fact, the assays carried out according to the Irwin test on the mouse show that the substances of the invention do not lead to death or convulsions in the animals up to doses of more than 1,000 mg.kg$^{-1}$.

These substances are thus particularly suited to the development of pharmaceutical compositions.

The pharmaceutical compositions of the invention contain an efficacious amount of at least one derivative of L-proline such as those defined above, in combination with an inert pharmaceutical vehicle.

Advantageous pharmaceutical compositions contain these derivatives alone or in combination with psychotropic medicines, anti-depressants, neuroleptics and L-dopa.

In view of their nootropic activity, these pharmaceutical compositions can be used particularly in the following therapeutic indications: disorders of memory, senile dementia, Alzheimer's Disease, Parkinson's Disease, schizophrenia, depression, peripheric neuropathies and motor neurone diseases.

The pharmaceutical compositions of the invention can be administered in different forms and by different routes, namely nasal, rectal and oral routes, and by injection.

In the case of administration by the oral route, recourse may be had in particular to tablets, pills, lozenges, gelatine capsules, drops and even liposomes. These compositions advantageously contain from 1 to 100 mg, and preferably from 2.5 to 50 mg, per dosage unit.

Other forms of administration comprise sterile or sterilizable solutions which can be injected by the intravenous, subcutaneous or intramuscular routes. Such solutions contain from 1 to 50 mg, and preferably from 0.5 to 50 mg, of the substance per dosage unit. As a guide, the dosage which may be used in man corresponds to the following doses: for example 5 to 300 mg/day may be administered to a patient in one or several doses.

The invention also relates to biological reagents, the active principles of which are constituted by the derivatives of L-proline defined above. These reagents can be used as references or for calibration purposes in studies of possible nootropic activity.

Other characteristics and advantages of the invention will become apparent in the examples which follow relating to the preparation of derivatives of L-proline and to the study of their nootropic activity.

EXAMPLE 1

Synthesis of cinnamoyl-glycyl-L-phenylalanyl-L-prolinamide corresponding to Formula VI

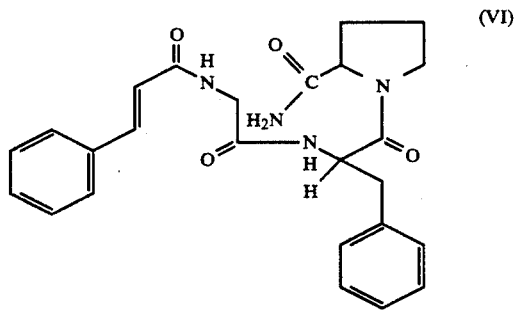

(VI)

This synthesis consists of five steps which were carried out as follows:

1) Preparation of t-Boc-L-phenylalanyl-L-prolinamide

The following compounds are used in the amounts indicated:

| | |
|---|---|
| t-Boc-L-phenylalanine. | 40 g |

| | |
|---|---|
| tetrahydrofuran | 200 ml |
| N-methylmorpholine | 21 ml |
| isobutyl chloroformate | 19.5 ml |
| 1-hydroxybenzotriazole | 23 g |
| dimethylformamide | 75 ml |
| L-prolineamide | 17.12 g |
| dimethylformamide | 75 ml | t-Box-L-phenylalanine (tertiary butoxycarbonyl-L-phenylalanine) was dissolved in tetrahydrofuran, the solution was cooled to −15° C. while being stirred magnetically and N-methylmorpholine was added, followed by isobutyl chloroformate. The reaction mixture was stirred for 5 to 10 minutes at low temperature, and then a pre-cooled solution of 1-hydroxybenzotriazole in dimethylformamide was added. The reaction mixture was stirred for a further 5 to 10 minutes before a pre-cooled solution of prolinamide in dimethyl formamide was added.

The mixture was stirred for about 1 hour at low temperature, then it was allowed to warm to room temperature and stirring was continued for about 14 hours.

The reaction mixture was diluted with ethyl acetate (about 800 ml) and then it was washed successively with a saturated, aqueous solution of sodium chloride (twice), a 5% aqueous solution of sodium bicarbonate (three times), a saturated, aqueous solution of sodium chloride (once), an aqueous solution of 0.5 N hydrochloride acid (three times) and a saturated, aqueous solution of sodium chloride (three times). The organic phase was dried over magnesium sulfate, filtered and then evaporated under reduced pressure. The residual syrup was triturated with petroleum ether in order to induce crystallization and the product obtained was filtered off, washed with petroleum ether and dried in a vacuum.

43.7 g of product were obtained. Thin layer chromatography (CHCl$_3$:MeOH:AcOH, 45:4:1) revealed a R$_f$ for the compound of 0.5.

2) Preparation of cinnamoyl-glycine methyl ester

| | |
|---|---|
| glycine methyl ester hydrochloride | 28 g |
| N-methylmorpholine | 39 ml |
| cinnamoyl chloride | 33 g |
| tetrahydrofuran | 250 ml |
| N-methylmorpholine | 35 ml |

Glycine methyl ester hydrochloride was suspended in tetrahydrofuran, the suspension was cooled to −5° C. to −10° C., and then half of the N-methylmorpholine was added. Cinnamoyl chloride was added immediately, followed by the other half of the N-methylmorpholine. The reaction mixture was stirred for 30 minutes at low temperature, then it was allowed to warm to room temperature and stirring was continued for 2 to 3 hours. After being diluted with ethyl acetate (about 750 ml) the solution was washed with water (three times), an aqueous solution of 0.5 N hydrochloric acid (three times) and finally with water. The organic phase was dried over magnesium sulfate, filtered and evaporated to dryness under reduced pressure. The residue was triturated with petroleum ether is order to induce crystallization. The product was left to stand for about 14 hours at 4° C., then it was filtered off and dried in a vacuum. It was used in the next step without further purification. 31 g of product were obtained.

3) Preparation of cinnamoyl glycine:

The following compounds were used in the amounts indicated:

| | |
|---|---|
| cinnamoyl-glycine ester | 31 g |
| methanol | 300 ml |
| sodium hydroxide (2 N in methanol) | 150 ml |

Cinnamoyl-glycine methyl ester was dissolved in methanol and a 2 N solution of sodium hydroxide in methanol was then added. The reaction mixture was stirred at room temperature for 2 hours, then it was diluted with water (300 ml). The pH of the mixture was adjusted to 1.5 with hydrochloric acid when the product precipitates. The reaction mixture was left to stand for about 14 hours at 4° C. in order for crystallization to be completed, the product was then filtered off, washed with water and dried in a vacuum. The yield is 23 g. The melting point of the product is 189° to 192° C. Thin layer chromatography (CHCl$_3$:MeOH:AcOH, 45:4:1) revealed a R$_f$ for the compound of 0.2.

4) Preparation of L-phenylalanyl-L-prolinamide trifluoracetate

The following compounds were used:

| | |
|---|---|
| t-Boc-phenylalanyl-L-prolineamide | 30 g |
| dichloromethane | 300 ml |
| trifluoroacetic acid | 300 ml | t-Boc-L-phenylalanyl-L-prolineamide was dissolved in dichloromethane and the solution was treated with trifluoroacetic acid for 30 minutes at room temperature. The solvent was evaporated under reduced pressure, the residue was taken up in toluene and the solution was reevaporated. The oily residue was triturated with ether in order to precipitate the product which was filtered off and dried in a vacuum. 33.1 g of product were obtained. Thin layer chromatography (CHCl$_3$:MeOH:AcOH, 45:4:1) revealed a R$_f$ for the compound of 0.3.

5) Preparation of cinnamoyl-glycyl-L-phenylalanyl-L-prolinamide

The reaction was carried out by using the following compounds in the amounts indicated:

| | |
|---|---|
| cinnamoyl-glycine | 20 g |
| dimethylformamide | 200 ml |
| 1-hydroxybenzotriazole | 16.3 g |
| dicyclohexylcarbodiimide | 20 g |
| L-phenylalanyl-L-prolin amide TFA | 33 g |
| dimethylformamide | 200 ml |
| N-methylmorpholine | 11 ml |

Cinnamoyl-glycine was dissolved in dimethylformamide, the solution was cooled to 0° C., then 1-hydroxybenzotriazole was added followed by dicyclohexylcarbodiimide. The reaction mixture was stirred for 1 hour at 0° C., then for 1 hour at room temperature.

During this time L-phenylalnyl-l-prolin amide trifluoroacetate was dissolved in dimethylformamide (200 ml). solution was cooled to 0° C. and treated with N-methylmorpholine. This solution was added to the solution of cinnamoylglycine active ester previously formed and the mixture was stirred at room temperature for about 14 hours. The reaction mixture was diluted with ethyl acetate (1.5 liters), filtered and washed with saturated sodium chloride solution (twice), a 5% aqueous solution of sodium bicarbonate (three times), a saturated sodium chloride solution (once), 0.5 N hydrochloric acid (three times) and finally with saturated sodium chloride solution (three times).

The organic phase was dried over magnesium sulfate, filtered and the solvent was evaporated under reduced pressure. The residue was redissolved in acetone, the solution was filtered and the filtrate was evaporated under reduced pressure. In order to remove residual dicyclohexylurea, the work-up procedure was repeated (twice). The product recovered (13.5 g) purified on silica gel (500 g) using dichloromethane containing from 1% to 5% methanol as eluant. The fractions containing the pure product were pooled and evaporated to dryness under reduced pressure. The residue was triturated with petroleum ether, filtered off and dried in a vacuum.

11.5 g of product were obtained with a melting point 95° C.-115° C. (This melting point range might be due to a cis-trans isomerization). Thin layer chromatography using (CHCl$_3$:MeOH:AcOH, 45:4:11 ) gave a R$_f$ of 0.4 and a R$_f$ of 0.8 was obtained using (n-BuOH:AcOH:-H$_2$O, 4:1:1). $[\alpha]_D = 49.62°$ (c=1, MeOH).

The product obtained was insoluble in water and is soluble to the extent of at least 1% to 5% in organic solvents such as methanol. chloroform, ethyl acetate and dimethylformamide.

EXAMPLE 2

Synthesis of 4-fluorocinnamoylglycyl-L-phenylalanine-L-prolinamide of formula VII

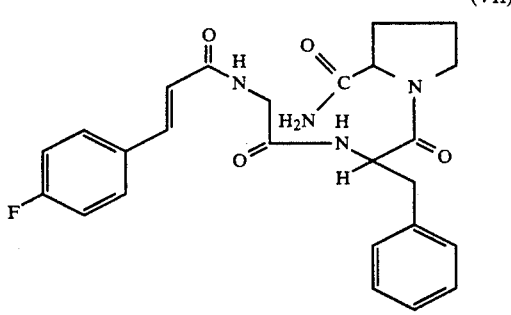

(VII)

1. 4-fluorocinnamoyl-glycine methyl ester

Following the general procedure described in example 1, step 2, for cinnamoyl-glycine methyl ester, glycine methyl ester hydrochloride (7.5 g) was suspended in tetrahydrofuran, cooled to 0° C., treated with N-methylmorpholine (8.4 ml, 1 equivalent), followed immediately by a precooled solution of 4-fluorocinnamic acid (10.0 g) in tetrahydrofuran, which had been preactivated by treatment with dicyclohexylcarbodiimide (12.4 g, 1 equivalent) and 1-hydroxybenzotriazole (9.2 g). After work-up, 4-fluorocinnamoyl-glycine methyl ester was obtained as a white solid which was used for the next step without further purification.

Yield:8.5 grams.

TLC:(CHCl$_3$:MeOH:AcOH, 45:4:1):R$_f$=0.8.

2. 4-fluorocinnamoyl-glycine

The product from the previous step (8.5 g) was saponified by treatment with sodium hydroxide in methanol, as described previously in example 1, step 3, for cinnamoyl-glycine.

Yield:3.4 grams.

TLC:(CHCl$_3$:MeOH:AcOH, 45:4:1):R$_f$=0.2.

3. 4-fluorocinnamoyl-glycyl-L-phenylalanyl-L-prolinamide

The product from the previous step (1.78 g) was coupled to L-phenylalanyl-L-prolinamide trifluoroacetate (3.0 g) through use of dicyclohexylcarbodiimide in the presence of 1-hydroxybenzotriazole. The product was obtained as a white solid after work-up.

Yield:1.4 grams.

TLC:(CHCl$_3$:MeOH:AcOH, 45:4:1):R$_f$=0.4.

MP:125° C.

EXAMPLE 3

Synthesis of 3,4-methylenedioxycinnamoyl-glycyl-L-phenylalanyl-L-prolinamide of formula VIII

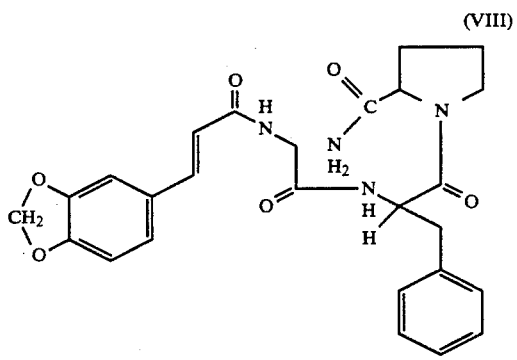

(VIII)

The product was synthesized using the same general procedures as those described previously for the cinnamoyl and 4-fluorocinnamoyl analogs.

1. 3,4-methylenedioxycinnamoyl-glycine methyl ester 3,4-methylenedioxycinnamic acid (15.0 g) was coupled with glycine methyl ester hydrochloride (9.78 g)

Yield:12.2 grams.

TLC:(CHCl$_3$:MeOH:AcOH,45:4:1)R$_f$=0.6

2. 3,4-methylenedioxycinnamoyl-glycine

The product from the previous step (12.2 g) was saponified as described previously.

Yield:7.2 grams.

TLC:(CHCl$_3$:MeOH:AcOH, 45:4:1): R$_f$=0.2 (n-BuOH:AcOH:H$_2$O, 4:1:1).

3. 3,4-methylenedioxycinnamoyl-glycyl-L-phenylalanyl-L-prolinamide

The product from the previous step (3.9 g) was coupled with L-phenylalanyl-L-prolinamide trifluoroacetate (5.55 g) to give the desired product after work-up.

Yield:1.3 grams.

TLC:(CHCl$_3$:MeOH:AcOH, 45:4:1):R$_f$=0.5.

Mp:92°–9320 C. (dec.).

EXAMPLE 4

Synthesis of 3,4,5-trimethoxycinnamoyl-glycyl-L-phenylalanyl-L-prolinamide of formula IX

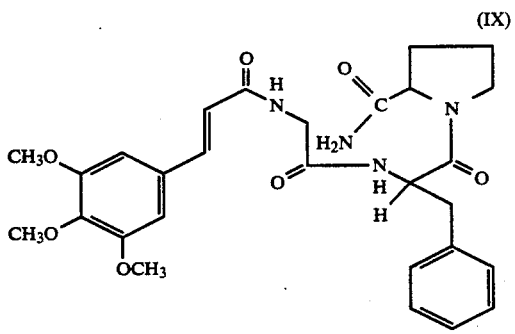

(IX)

The same general procedures were used as those outlined above for 4-fluorocinnamoyl-glycyl-L-phenylalanyl-L-prolinamide and the cinnamoyl analog described previously.

1. 3,4,5-trimethoxycinnamoyl-glycine methyl ester 3,4,5-trimethoxycinnamic acid (15.0 g) was coupled with glycine methyl ester hydrochloride (7.9 g).

Yield:13.2 grams.

TLC:(CHCl$_3$:MeOH:AcOH, 45:4:1):R$_f$=0.7.

2. 3,4,5-trimethoxycinnamoyl-glycine

The product from the previous step (13.2 g) was saponified as described previously.

Yield:5.8 grams.

TLC:CHCl$_3$:MeOH:AcOH, 45:4:1):R$_f$=0.2; (n-BuOH:AcOH:H$_2$O,4:1:1):R$_f$=0.6.

3. 3,4,5-trimethoxycinnamoyl-glycyl-L-phenylalanyl-L-prolinamide

The product from the previous step (3.0 g) was coupled with L-phenylalnyl-L-prolinamide trifluoroacetate (4.0 g) to give the desired product after work-up.

Yield:2.3 grams.

TLC:(CHCl$_3$:MeOH:AcOH, 45:4:1):R$_f$=0.7

Mp:122° C.

EXAMPLE 5

Synthesis of cinnamoyl-glycyl-L-leucyl-L-prolinamide of formula X

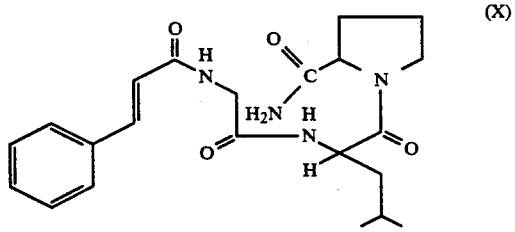

(X)

1. t-butyloxycarbonyl-L-leucyl-L-prolinamide

Following the general procedure described previously for t-butyloxycarbonyl-L-phenylalanyl-L-prolinamide, a solution of t-butyloxycarbonyl-L-leucine (32.64 g), in tetrahydrofuran was activated by treatment with N-methylmorpholine (18.22 ml), followed by isobutylchloroformate (16.99 ml) at −5° C. After 15 minutes, L-prolinamide hydrochloride (15.0 g) was added as a solution in dimethylformamide, followed by N-methylmorpholine (18.22 ml) and the mixture stirred overnight at room temperature. The reaction was worked up as described previously to give the desired product, which was used for the next step without further purification.

Yield:30.0 grams.

TLC:CHCl$_3$:MeOH:AcOH, 85:10:5:R$_f$=0.6.

2. L-leucyl-L-prolinamide trifluoroacetate

The product from the previous step (30.0 g) was deprotected as described previously, by treatment with trifluoroacetic acid:methylene chloride (1:1, 150 ml) at room temperature. Evaporation of the reaction mixture and trituration with ether gave the desired product which was used for the next step without further purification.

Yield:29.5 grams.

TLC:(n-BuOH:AcOH:H$_2$O, 4:1:1):R$_f$=0.6; (CHCl$_3$:MeOH:AcOH, 85:15:5): R$_f$=0.2.

3. Cinnamoyl-glycine methyl ester

Cinnamic acid (38.0 g) was coupled to glycine methyl ester hydrochloride in dimethylformamide by treatment with dicyclohexylcarbodiimide (52.84 g) and 1-hydroxybenzotriazole (39.24 g), followed by N-methylmorpholine (37.56 ml). The reaction mixture was stirred overnight at room temperature and then worked up in the usual manner to give the desired product.

Yield:34.5 grams.

TLC:(CHCl$_3$:MeOH:AcOH, 85:15:5): R$_f$=0.8.

4. Cinnamoyl-glycine

The product from the previous step (35.0 g) was saponified by treatment with sodium hydroxide (7.4 g) in methanol for 1 hour at room temperature. Work-up in the usual manner gave the desired product which was used for the next step without further purification.

Yield:30.2 grams.

TLC:(n-BuOH:AcOH:H$_2$O, 4:1:1): Rf=0.4; (CHCl$_3$:MeOH:AcOH, 85:15:5): Rf=0.8.

5. Cinnamoyl-glycyl-L-luecyl-L-prolinamide

The product from the previous step (15.0 g) was coupled with L-leucyl-L-prolinamide trifluoroacetate (24.42 g) in dimethylformamide using dicylcohexylcarbodiimide (15.05 g) and 1-hydroxybenzotriazole (11.2 g), followed by N-methylmorpholine (7.37 ml). After overnight reaction, the reaction mixture was worked up in the usual manner to give the desired product as a white solid.

Yield:5.8 grams.

TLC:(CHCl$_3$:MeOH:AcOH, 85.15:5): R$_f$=0.6.

Mp:107°-107.5° C.

EXAMPLE 6

Synthesis of benzoyl-glycyl-L-phenylalanyl-L-prolinamide of formula XI

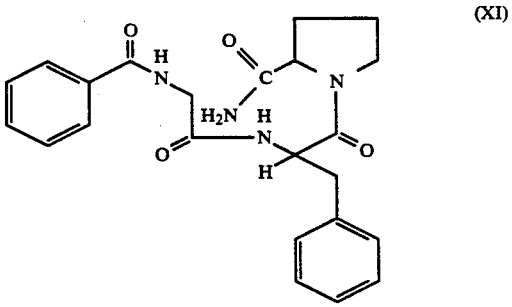

(XI)

1. Benzoyl-glycine-t-butyl ester

Following the same general procedure described previously for cinnamoyl-glycine-methyl ester, glycine-t-butyl ester. MCl (10.88 grams) was dissolved in dimethyl formamide (approximately 100 ml), cooled to 0° C. and treated with N-methylmorpholine (9.04 ml, 1 equivalent) followed immediately by a pre-cooled solution of benzoic acid (7.94 grams) in ethyl acetate (approximately 75 ml) which had been pre-activated by treatment with N-methylmorpholine (9.04 ml) followed by isobutyl chloroformate (8.4 ml) at −20° C. After work-up, benzoyl-glycine-t-butyl ester was obtained as a white solid which was used for the next step without further purification.

Yield:8.1 grams.
TLC:(CHCl$_3$:MeOH:AcOH, 85:10:5): Rf=0.9.

2. Benzoyl-glycine

The product from the previous step (8.1 grams) was treated with trifluoroacetic acid (90 ml) for one hour at room temperature. After evaporation of the trifluoroacetic acid and trituration of a residue with ether, the product was obtained as a white solid which was used without further purification.

Yield:5.2 grams.
TLC:(CHCl$_3$:MeOH:AcOH, 85:10:5): Rf=0.35.
M.p.:181°-184° C.

3. Benzoyl-glycyl-L-phenylalanyl-L-prolinamide

The product from the previous step (2.61 grams), as a solution in dimethylformamide) was coupled to L-phenylalanyl-L-prolinamide trifluoroacetate (5.5 grams, as a solution in tetrahydrofuran) by the mixed anhydride procedure. The product was obtained as a white solid after work-up.

Yield:1.67 grams.
TLC:(CHCl$_3$:MeOH:AcOH, 85:10:5): Rf=0.6.
M.p.:95°-113° C.

EXAMPLE 7

Synthesis of phenylacetyl-glycyl-L-phenylalanyl-L-prolinamide of formula XII

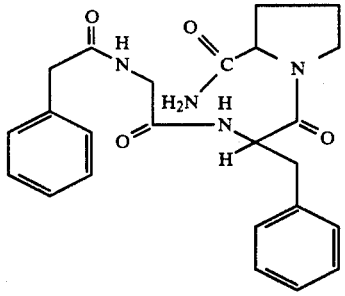

(XII)

1. Phenylacetyl-glycine-t-butyl ester

Following the procedure described for benzoyl-glycine-t-butyl ester, a solution of phenylacetic acid (11.44 grams) in ethyl acetate (approx. 100 ml) was activated by the mixed anhydride method using N-methylmorpholine (11.66 ml) followed by isobutyl chloroformate (10.89 ml) at −20° C. and coupled with glycine t-butyl ester.HCl (14.04 g) in methylene chloride (approx. 150 ml) which had been neutralized by addition of N-methylmorpholine (11.66 ml). After work-up, the product was obtained as an oil which was used for the next step without further purification.

2. Phenylacetyl-glycine

The product from the previous step was treated with trifluoroacetic acid (250 ml) for 1 hour at room temperature. Evaporation of the reaction mixture and trituration of the residue with ether gave the desired product as a white solid.

Yield:6.8 grams.
TLC:(CHCl$_3$:MeOH:AcOH, 85:10:5): Rf=0.25.
M.p.:132°-135° C.

3. Phenylacetyl-glycyl-L-phenylalanyl-L-prolinamide

Following previously described procedures, phenylacetyl-glycine (4.0 grams, as a solution in tetrahydrofuran) was coupled with L-phenylalanyl-L-prolinamide trifluoroacetate (7.87 grams, as a solution in methylene chloride) by the mixed anhydride procedure. The product was obtained as a white solide after work-up.

Yield:5.05 grams.
TLC:(CHCl$_3$:MeOH:AcOH, 85:10:5):Rf=0.7.
M.P.:81°-98° C.

EXAMPLE 8

Preparation of the L-proline derivative corresponding to Formula XIII.

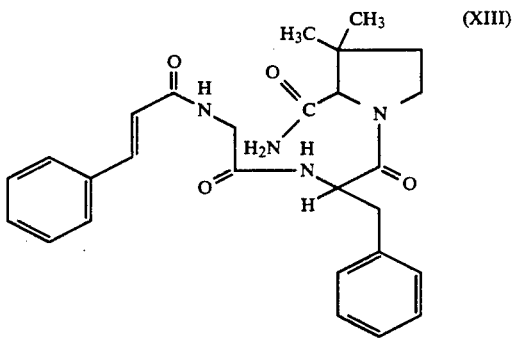

(XIII)

The procedure employed is that described in Example 1 except that dimethyl prolineamide is used. This derivative is synthesized by appropriate modification of the method described in patent UK 1.523598 relating to L-pyroglutamoyl-L-histidyl-L-3,3 dimethyl prolineamide.

EXAMPLE 9

Pharmacological studies

1) Irwin test:

A volume of 0.25 ml/20 g of body weight of a suspension of the compound of the invention in 5% gum arabic is administered to male mice of the NMRI strain by the i.p. route.

The control animals received only the 5% suspension of gum arabic.

Changes in behaviour, neurotoxicity symptoms, the diameter of the pupil and the rectal temperature are recorded in the standardized observation schedule according to Irwin in Psychopharmacologia, 1968, 13, 222-257.

These observations were made at 15, 30, 60, 120 and 180 minutes after injection and 24 hours later.

The compounds of the invention were studied at doses of 1024, 512 and 256 mg.kg$^{-1}$.

At the doses studied the animals suffered neither death nor convulsions.

With compound corresponding to Formula VI, slight sedation (1 mouse/3) or excitation (1 mouse/3) was observed between 1 and 2 hours after the administration of 1024 mg.kg$^{-1}$, accompanied by a moderate ptosis (3 mice/3) and hypothermia (2 mice/3).

At a dose of 512 mg.kg$^{-1}$, the compound corresponding to Formula VI caused only a slight hypothermia. At 256 mg.kg$^{-1}$, no difference from the control animals was observed.

2) Test of passive avoidance:

a) Amnesia induced by scopolamine:

The procedure described by Glick and Zimmerberg in Behavioural Biology, 1972, 7: 245-254 and by Lenegre et al in Pharmacol. Biochem. Behav., 29 (3) 1988 were used.

The mouse is introduced into the illuminated compartment of a two-compartment box. When it crosses into the darker component its paws receive electric shocks of 0.3 mA until it returns into the illuminated compartment (Assay 1).

When the mouse is returned to the box 24 hours later (Assay 2), it avoids going into the darker component. An i.p. injection of scopolamine (1 mg.kg$^{-1}$) 30 minutes before Assay 1 reduces the memory of this experience as is reflected in the delay of the reaction of the mouse before it crosses to the darker compartment in Assay 2.

The compounds of the invention were tested at the following doses: 0.25, 1,4,8 and 16 mg.kg$^{-1}$ and were administered by the i.p. or the oral route 60 minutes before S1.

Piracetam was used as reference substance.

The results obtained with the compounds of the Examples, show that said compounds, when administered by the i.p. or one route 60 mn. before the assay, do not bring about any change in the latent periods for crossing into the dark compartment or for escaping from this compartment during Assay 1.

Under the same experimental conditions, piracetam does not produce any effect on the two parameters measured during Assay 1.

During Assay 2, it is observed that scopolamine, when administered 30 minutes before Assay 1, brings about a diminution of the time which elapses before the mouse crosses into the dark compartment.

When administered by the i.p. route 60 minutes before Assay 1, the product of Example 1 antagonizes the effects of scopolamine at doses of 1, 4 and 16 mg/kg, the effect being significant at a dose of 1 mg/kg.

In the same experiment, piracetam has an antagonistic effect on the amnesia induced by scopolamine but at a dose of 512 mg/kg, a result which clearly demonstrates the advantageous properties of the compounds of the invention which are active at a lower dose.

Similarly, assays carried out by oral administration of the compounds of the invention have shown that they exert a strongly antagonistic effect on the amnesia induced by scopolamine compared with that of compounds known to the state of the art.

The products of examples 1, 2, 3, 6 and 7 are active in this test at 2, 8 and 32 mg/kg. This activity is significant even at a dose of 2 mg/kg. The importance of the compounds of the invention is emphasized by the fact that piracetam is active in this test but at the markedly higher dose of 2048 mg/kg.

b) Amnesia induced by diazepam:

A volume of 0.25 ml/20 g of body weight of the compound of Example 1 (suspension in 5% gum arabic) is administered to mice of the NMRI strain or, in the case of the reference substance, an aqueous solution of piracetam or of diazepam (5% suspension in gum arabic) is administered. The control animals receive only injections of the vehicle (suspension of gum arabic).

The test is carried out at indicated above for the induction of amnesia by the injection of scopolamine, with exception that this latter is replaced by diazepam. An injection of diazepam by the i.p. route 30 minutes before Assay 1 at a dose of 1 mg.kg$^{-1}$ reduces memory in a significant manner as is shown by the diminution of the reaction time in the mouse for crossing to the dark compartment during Assay 2.

A considerable reduction of amnesia at a lower dose of product is observed with the compounds of the invention.

Thus, it is observed that the product of Example 1 studied at doses of 0.25, 1 and 4 mg.kg$^{-1}$ and administered 60 minutes before Assay 1, antagonizes the effect of diazepam in a dose-dependent manner.

This effect appears to be statistically significant when 4 mg.kg$^{-1}$ of the product are administered.

Amnesia is reduced by agents exerting a nootropic action such as piracetam and its derivatives when they are used in these assays at a dose of 512 mg.kg$^{-1}$ by the i.p. route 60 minutes before Assay 1.

These results show that, at low doses, the compounds of the invention counteract the amnesia induced both by scopolamine and by diazepam when they are used under similar experimental conditions.

3) Antagonism of sleep induced by barbiturates:

A compound of the invention is administered orally at doses of 2, 8 and 32 mg.kg$^{-1}$ to mice of the NMRI strain one hour before the intraperitoneal administration of barbital at a dose of 50 mg/kg.

The compound of Example 1 significantly diminishes the duration of sleep, compared with that in a control group, at doses of 2 and 8 mg/kg.

4) Potentiation of the effects of L-dopa:

A compound of the invention is adiministered orally at doses of 2, 8 and 32 mg/kg to NMRI mice one hour before the intraperitoneal administration of 150 mg/kg of L-dopa. This dose of L-dopa does not bring about any behavioural change in the control group. At doses of 8 and 32 mg/kg the product of Example 1 induces behavioural changes in the treated animals such as rapid running and jumping.

The sum total of these results demonstrates the advantageous properties of the compounds of the invention, more especially as the active principles of medicines exerting a nootropic effect.

5) Effect on adenohypophyseal hormone secretions

Male rats received 2 mg/kg, 8 mg/kg, or 32 mg/kg IP of product of example 1 in arabic gum (2.5%) and 32 mg/kg IP of products of examples 2 and 3. Rats were killed 30 min. later by decapitation and plasma samples were aliquoted and kept frozen (−20° C.) until assays. Before the experiments, the rats have been accustomed to handling to avoid any stress effect.

Hormones were assayed using radioimmunoassays for prolactin, GH and TSH.

Prolactin levels were slightly increased with the products of example 1 but in a dose dependent way. TSH levels are very slightly increased at 8 mg/kg. Products of examples 2 and 3 have no activity at all at 32 mg/kg on prolactin TSH and GH levels.

I claim:

1. A L-proline derivative of the formula I:

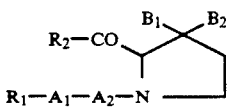

or a pharmacologically acceptable salt thereof, wherein $R_1$ is a group corresponding to Formula II:

in which

R is selected in group consisting of a carbonyl radical CO—, an acyl radical Y—CO— or an oxy-acyl radical O—Y—CO—, Y being an alkyl or alkenyl group containing from 1 to 4 carbon atoms and, Z represents in the ortho and/or ortho' and/or meta and or meta' and/or para positions hydrogen or a substituent chosen from among halogen atoms, $CF_3$ group, alkyl or alkoxy radicals containing from 1 to 4 carbon atoms, and in the case of 2 neighbouring substituents, an alkylenedioxy group, in which the alkyl group contains from 1 to 3 carbon atoms, $R_2$ is a NH2 or OH radical or functional derivative $A_1$ and $A_2$, identical or different, are naturally occurring amino acid residues, and $B_1$ and $B_2$, identical or different, represent a hydrogen atom or a methyl group, with the provisos that on the one hand $A_1$ be different from a phenylalanyl residue when $B_1$ and $B_2$ represent H, $R_2$ represents OH, $R_1$ is benzoyl and $A_2$ is an alanyl residue, and, on the other hand, that $A_2$ be different from a proline residue, when $B_1$ and $B_2$ represent H, $R_2$ represents —OH or —NH2, or the functional derivatives thereof and R is —CO— or —Y—CO, with Y being an alkyl group.

2. The derivative according to claim 1, wherein Z in Formula II is a hydrogen atom.

3. The derivative according to claim 1, wherein Z in Formula II is a halogen atom selected from among chlorine and fluorine, a $CF_3$ group, an alkoxy radical chosen from among methoxy and ethoxy, and in the case of two neighbouring substituents, an alkylenedioxy radical chosen from among 3,4-methylene and 3,4-ethylenedioxy.

4. The derivative according to claim 1 wherein in Formula II, R is chosen from among the groups CO—, $CH_2$—CO—, $CH_2$—$CH_2$—CO, $CH_2$—$CH_2$—$CH_2$—CO, CH=CH—CO— and O—$CH_2$—CO.

5. The derivative according to claim 1, wherein $R_1$ is a cinnamoyl group, said group being optionally substituted.

6. The derivative according to claim 1, wherein $A_1$ is a glycyl residue.

7. The derivative according to claim 1, wherein $A_1$ is chosen from among the residues L-alanyl and L-valyl.

8. The derivative according to claim 1, wherein $A_1$ is selected in the group consisting of glycyl, L-alanyl and L-valyl and $A_2$ from among the residues glycyl, L-phenylalanyl, L-histidyl, L-leucyl, L-valyl and L-alanyl.

9. A derivative of L-proline selected from the group consisting of: cinnamoyl-glycyl-L-phenylalnyl-L-prolinamide, 4-fluorocinnamoyl-glycyl-L-phenylalanine-L-prolinamide, 3,4-methylenedioxycinnamoyl-glycyl-L-prolinamide, 3,4,5-trimethoxycinnamoyl-glycyl-L-phenylalanyl-L-prolinamide, cinnamoyl-glycl-L-leucyl-L-prolinamide, benzoyl-glycyl-L-phenylalanyl-prolinamide, phenylacetyl-glycyl-L-phenylalanyl-L-prolinamide and, cinnamoyl-glycyl-L-phenylalanyl-L-3,3'-dimethyl-prolinamide.

10. A pharmaceutical composition in dosage unit form, comprising, in combination, a pharmaceutically acceptable carrier and a psychotropic amount of at least one derivative of the derivative according to claim 1.

11. The composition of claim 10 wherein said L-proline derivative is in association with another active principle selected in the group consisting of psychotrophic medicines, anti-depressants, neuroleptics and L-dopa.

12. The composition according to claim 10 which is in the form of a lozenge, tablet, gelatin capsule, drop, pill, liposome and containing from 1 to 100 mg of the derivative per dosage unit.

13. The composition according to claim 12, wherein the dosage unit of said derivative is about 2.5 to 50 mg.

14. The composition according to claim 10 which is a solution of the derivative in a concentration of bout 1 to 50 mg per dosage unit.

15. The composition 14, which is a solution of the derivative in a concentration of 0.5 to 50 mg per dosage unit.

16. The L-proline derivative of claim 1 wherein $R_2$ is a NH2 or OH radical or functional derivative of OH selected from the group consisting of an ester and an ether.

17. The method of claim 1, wherein the administration of the composition is by the oral, rectal or nasal route or by injection.

18. A method of treating amnesia comprising administering to a patient in need of such treatment the pharmaceutical composition according to claim 10, in an amount sufficient to effect said treatment.

* * * * *

UNITED STATES PATENT AND TRADEMARK OFFICE
CERTIFICATE OF CORRECTION

PATENT NO. : 5,212,158
DATED : May 18, 1993
INVENTOR(S) : Fiez Vandai

It is certified that error appears in the above-identified patent and that said Letters Patent is hereby corrected as shown below:

On title page, item [19] "Fiez Vandai" should read --Fiez-Vandal--
On title page, item [75] "Fiez Vandai" should read --Fiez-Vandal--

Col. 2, line 28, delete "$A_{11},A2$" and insert --$A_1,A_2$--.

Col. 8, line 67, delete "$92°-9320\ C$" and insert --$92-93°C$--.

Col. 10, line 48, delete "$107-107.5°C$" and insert --$107.5-116.5°C$--.

Col. 11, line 3, delete "MCl" and insert --HCl--.

IN THE CLAIMS:
Col. 15,
Claim 4, line 3, delete "$CH_2-CH_2-CH$", line 4, delete "$_2-CO$" and insert --$CH_2-CH_2-CH_2-CO$--.

Signed and Sealed this

Third Day of May, 1994

Attest:

BRUCE LEHMAN

Attesting Officer    Commissioner of Patents and Trademarks